(12) United States Patent
Woolley (10) Patent No.: US 8,703,067 B2
(45) Date of Patent: Apr. 22, 2014

(54) AIR TREATMENT AGENT DISPENSER WITH IMPROVED ODOUR SENSOR FUNCTIONALITY

(75) Inventor: Simon Woolley, Hull (GB)

(73) Assignee: Reckitt & Colman (Overseas) Limited, Slough, Berkshire (GB)

( * ) Notice: Subject to any disclaimer, the term of this patent is extended or adjusted under 35 U.S.C. 154(b) by 0 days.

(21) Appl. No.: 13/501,854

(22) PCT Filed: Oct. 18, 2010

(86) PCT No.: PCT/GB2010/051747
§ 371 (c)(1),
(2), (4) Date: May 9, 2012

(87) PCT Pub. No.: WO2011/045615
PCT Pub. Date: Apr. 21, 2011

(65) Prior Publication Data
US 2012/0237404 A1    Sep. 20, 2012

(30) Foreign Application Priority Data

Oct. 16, 2009 (GB) .................................. 0918140.5

(51) Int. Cl.
| | | |
|---|---|---|
| *A61L 9/00* | (2006.01) | |
| *A01N 25/00* | (2006.01) | |
| *A61L 9/03* | (2006.01) | |
| *A61L 9/04* | (2006.01) | |
| *B01B 1/04* | (2006.01) | |

(52) U.S. Cl.
CPC . *A01N 25/00* (2013.01); *A61L 9/00* (2013.01); *A61L 9/03* (2013.01); *A61L 9/037* (2013.01); *A61L 9/04* (2013.01); *B01B 1/04* (2013.01)
USPC .......................................... 422/306; 422/307

(58) Field of Classification Search
CPC ............ A01N 25/00; A61L 9/00; A61L 9/03; A61L 9/037; A61L 9/04; B01B 1/005
USPC .................... 422/1, 5, 28, 123–125, 306–307
See application file for complete search history.

(56) References Cited

FOREIGN PATENT DOCUMENTS

| EP | 2111875 A1 | 10/2009 |
|---|---|---|
| GB | 2405097 A1 | 2/2005 |

(Continued)

OTHER PUBLICATIONS

International Search Report dated Feb. 3, 2011 for PCT/GB2010/051747.

(Continued)

*Primary Examiner* — Monzer R Chorbaji
(74) *Attorney, Agent, or Firm* — Norris McLaughlin & Marcus PA (57) ABSTRACT

A device for evaporating a volatile air treatment agent from a replaceable refill is described herein, the device comprises: a housing with at least one exit orifice for evaporated air treatment agent to exit the device; receiving means within said housing to releasably receive and secure the refill to the device; electrical heating means within said housing; control means; and chimney means within said housing having a lower orifice and an upper orifice to define a first airflow channel therebetween; an airborne agent detector means operable to detect airborne agents in the air, wherein said means are provided with at least one aperture to the exterior of the device to permit, in use, air from outside of the device to enter said airborne agent detector means; wherein the refill for use with the device comprises: a reservoir portion for holding a quantity of volatile air treatment agent; and a wick having a proximal end within the reservoir portion substantially adjacent a base of said reservoir portion and having a distal end extending above the reservoir portion; and wherein the device is configured such that, in use, the securing means are adapted to hold the refill such that the distal end of the wick is located within the chimney means; characterized in that a second airflow channel is provided between said at least one aperture of the airborne agent detector means and said exit orifice.

31 Claims, 1 Drawing Sheet

(56) References Cited

FOREIGN PATENT DOCUMENTS

| | | | |
|---|---|---|---|
| GB | 2445731 | A | 7/2008 |
| JP | 2004141618 | A | 5/2004 |
| JP | 3988909 | A2 | 10/2007 |
| JP | 3988909 | B2 | 10/2007 |
| WO | 2004037304 | A1 | 5/2004 |
| WO | 2005018690 | A1 | 3/2005 |
| WO | 2006044416 | A2 | 4/2006 |
| WO | 2008059210 | A1 | 5/2008 |
| WO | 2008068486 | A2 | 6/2008 |
| WO | 2008128018 | A1 | 10/2008 |
| WO | 2009044123 | A1 | 4/2009 |
| WO | 2009060205 | A1 | 5/2009 |
| WO | 2009060212 | A2 | 5/2009 |
| WO | WO 2009/060212 | A2 * | 5/2009 |
| WO | 2009090415 | A2 | 7/2009 |

OTHER PUBLICATIONS

GB Search report for GB0918140.5 dated Feb. 17, 2010.
Written Opinion of the International Searching Authority for PCT/GB2010/051747 dated Feb. 3, 2011.
International Search Report dated Feb. 3, 2011 for PCT/GB2010/051749.
GB Search report for GB0918119.9 dated Feb. 17, 2010.
Written Opinion of the International Searching Authority for PCT/GB2010/051749 dated Feb. 3, 2011.
International Search Report dated Mar. 25, 2011 for PCT/GB2010/051753.
GB Search report for GB0918128.0 dated Feb. 17, 2010.
Written Opinion of the International Searching Authority for PCT/GB2010/051753 dated Mar. 25, 2011.
International Search Report dated Feb. 18, 2011 for PCT/GB2010/051750.
GB Search report for GB0918138.9 dated Feb. 17, 2010.
Written Opinion of the International Searching Authority for PCT/GB2010/051750 dated Feb. 18, 2011.
"The How and Why of Electronic Noses", H. Troy Nagle, IEEE Spectrum, pp. 1-22, Sep. 19, 1998 (XP002616922).
English language abstract for JP2004141618 A (dated May 20, 2004).
English language translation of JP3988909 B2 (dated Oct. 10, 2007).

* cited by examiner

AIR TREATMENT AGENT DISPENSER WITH IMPROVED ODOUR SENSOR FUNCTIONALITY

This is an application filed under 35 USC 371 of PCT/GB2010/051747.

FIELD OF THE INVENTION

The present invention relates to an electrical emanation device that is configured to adapt the emanation of a fluid into the surrounding environment based on a determination of the characteristics of the surrounding environment and particularly, but not exclusively, for the emanation of air treatment agents in the form of air treatment agents such as fragrances, deodorizing and/or pest control materials.

BACKGROUND

Devices are known in which a bottle of volatile liquid has an upwardly projecting wick and a heater is located in the vicinity of the upper end of the wick to accelerate the evaporation of volatile liquid from the wick. The bottle, wick and heater are retained within a housing which carries an electric plug. To operate the heater the device is plugged into a wall socket. Devices of this type commonly claim to allow control of the rate of evaporation of the volatile liquids, for example, by varying the distance between the heater and the wick.

Known prior art devices suffer from the drawback of efficiency and convenience. Typically the user has to manually change the apparatus from "normal" to "boost" mode, and then to switch it back to "normal" mode when this effect is no longer necessary (e.g. when the room is empty, or at night). Given the typical location of sources of electrical supply on walls (at a low level near the floor) or placement of electrical devices, this makes the switching process inefficient and inconvenient.

Timed devices are available which are configured to release air treatment agent at predefined time periods but these device are not capable of dynamically adjusting their operation to take account of changes in the surrounding environment.

In order to overcome some of the drawbacks associated with a device having a timer function, devices consisting of a combination of a timed functional with a motion sensor functional have been made available and go some way to addressing this problem, however, increased motion surrounding the device does not necessarily linearly equate to a need for increased air treatment agent.

To improve the known devices yet further to make them truly adaptive to their surrounding environment it has been suggested that an odour sensor could be included with such devices such that when the device's 'electronic nose' detects malodour or the like air treatment agent could be emanated, however, such devices are fraught with sensitivity and reliability issues which renders them largely unsuitable for mass commercialisation.

There is a need, therefore, for a device which overcomes the defects of the prior art.

SUMMARY OF INVENTION

According to a first aspect of the present invention there is provided therefore a device for evaporating a volatile air treatment agent from a replaceable refill, the device comprising:

a housing with at least one exit orifice for evaporated air treatment agent to exit the device;
receiving means within said housing to releasably receive and secure the refill to the device;
electrical heating means within said housing;
control means; and
chimney means within said housing having a lower orifice and an upper orifice to define a first airflow channel therebetween;
an airborne agent detector means operable to detect airborne agents in the air, wherein said means are provided with at least one aperture to the exterior of the device to permit, in use, air from outside of the device to enter said airborne agent detector means;
wherein the refill for use with the device comprises:
a reservoir portion for holding a quantity of volatile air treatment agent; and
a wick having a proximal end within the reservoir portion substantially adjacent a base of said reservoir portion and having a distal end extending above the reservoir portion;
and wherein the device is configured such that, in use, the securing means are adapted to hold the refill such that the distal end of the wick is located within the chimney means;
characterised in that a second airflow channel is provided between said at least one aperture of the airborne agent detector means and said exit orifice.

Preferably the housing comprises a bottom wall, a top wall remote therefrom and one or more side walls therebetween. The one or more side walls preferably consist of a front wall, a rear wall opposed thereto and a left side wall and a right side wall between said front and rear walls. The exit orifice(s) is preferably provided in the top wall and/or in the side wall(s) at a position substantially adjacent to the top wall such that air treatment agent emanated from the device, in use, is directed in a generally upward direction or a generally upward and forward direction that is generally perpendicular to the top wall of the housing.

Preferably the at least one aperture for the airborne agent detector means is spaced away from the exit orifice(s). In one preferred arrangement the at least one aperture may be located in a housing wall that is substantially perpendicular with the housing wall of the exit orifice. In an alternatively preferred arrangement the at least one aperture may be located in a housing wall that is substantially opposite to the housing wall of the exit orifice(s). More preferably the at least one aperture is located in the side wall(s) or rear wall of the housing adjacent or substantially adjacent to the bottom wall.

Preferably the second airflow channel is substantially completely separate from the first airflow channel, such that to the extent that there is any intersection of the two airflow channels said intersection is at or adjacent to the upper orifice.

Any intersection between the first airflow channel and the second airflow channel may be facilitated by a cut-out portion or the like in the first airflow channel.

Alternatively the second airflow channel may be substantially contiguous with the first airflow channel, such that the intersection between the two airflow channels is at or adjacent to the lower orifice.

As a further alternative the second airflow channel may be completely separate from and does not intersect with the first airflow channel, wherein said second airflow channel only permits the passage of air between said at least one aperture of the airborne agent detector means and said exit orifice.

As a yet further alternative the second airflow channel may be completely separate from and does not intersect with the first airflow channel, wherein said second airflow channel is present to only encourage the passage of air through said at least one aperture of the airborne agent detector means and past said airborne agent detector means and into the interior of the housing. In this arrangement there is no defined second airflow channel within the device once the airflow has passed the airborne agent detector means, the airflow is left to find its own way through the device toward the exit orifice.

The above-mentioned arrangements may be advantageous as the second airflow channel may permit a greater quantity of air to be drawn into and/or past the airborne agent detector means such that it is able to analyse a broader cross-section of the air surrounding the device to determine whether it is appropriate to emanate or increase the emanation rate of air treatment agent from the refill. During the operation of the device, the heat emitted in emanating the air treatment agent may also assist in driving airflow through the second airflow channel.

The second airflow channel may be provided with a tortuous pathway at or adjacent its intersection with the first airflow channel or at or adjacent the exit orifice such that any air treatment agent condensing in said second airflow channel will not be permitted to travel down the channel toward to the airborne agent detector means and risk the possible contamination and/or saturation thereof.

The second airflow channel may be provided with a filter membrane at or adjacent its upper extremity such as at its intersection with the first airflow channel or at or adjacent the exit orifice, wherein said filter membrane is configured to prevent or substantially prevent particulate contamination of the airborne agent detector means whilst allowing gas diffusion therethrough such that any air treatment agent condensing in or near said second airflow channel will not be permitted to travel down the channel toward to the airborne agent detector means and risk the possible contamination and/or saturation thereof. The filter membrane may be a plastics material with suitable diffusion properties such as a poly ethylene membrane.

If the device is provided with more than one airborne agent detector means and said plurality of detector means are spaced apart from each other within the housing, a respective airflow channel may be provided for each of said detector means.

In a preferred arrangement of the present invention the exit orifice of the housing is the upper orifice of the chimney means.

The chimney means may be rotatable relative to the housing to permit user-controlled alteration of the heat that is passed from the heating means toward the wick of a refill in use of the device.

Preferably the chimney means has an inner surface intended to face the wick of the refill that is substantially circular in cross-section, and preferably the wick of the refill has an outer surface that is substantially circular in cross-section with a small diameter than that of the inner surface of the chimney means such that when a refill is secured in position within the device by the receiving means; for the avoidance of doubt reference here to cross-section is where said cross-section is taken substantially perpendicular to the longitudinal axis of the wick/chimney means.

Preferably the exterior surface of the chimney means is substantially circular in cross-section, wherein said cross-section is taken substantially perpendicular to the longitudinal axis of said means.

The heating means is preferably located adjacent the chimney means. The chimney means may be provided with cut-out portions in registration with the heating means, whereby the ability of the chimney means to be rotated by a user permits a user to rotate the chimney means relative to the heating means, thus altering whether the cut-out portion or non-cut-out portion of the chimney means is between the wick and the heating means which affects the amount of heat directed toward the wick thereby.

The second airflow channel may be provided with a cut-out portion adjacent to the heating means to permit, in use, heat from said means to enter the channel and increase the airflow therethrough.

The chimney means is preferably made from a plastics material, and preferably from a plastics material that is a good thermal conductor such as nylon or polypropylene.

Preferably the heating means is fixed in position within the device such that it remains at a predetermined distance from the chimney means.

Alternatively, the heating means may be laterally movable toward and away from the chimney means in coordination with the rotation of the chimney means which may increase the performance of the device.

The heating means may be provided in any suitable form such as a bar heater or at least one point source resistor. Preferably the heating means is provided in the form of at least one electrical resistor, such as a thermistor. Preferably, at least one electrical resistor is used in the device of the present invention as the heating means.

The electrical power applied to the device may by provided by any suitable form, such as by mains electricity, batteries or solar cells. However, due to the power demands of the heating means and airborne agent detector mains electricity is preferred.

Where the device is intended for use with mains electricity, the device may be provided with plug formations configured to engage the openings in a mains electrical socket.

Where the device is provided with the plug formations, the formations are located toward a rear-facing wall of the housing and, in this arrangement, the receiving means can be located in a lower-facing aspect of the housing.

The device may be provided with variance means that directly or indirectly engage or communicate with the rotatable chimney means to permit a user of the device to rotate the chimney means in order to alter, in use, the temperature applied from the heating means to the wick of the refill, thus altering the rate of emanation of the volatile liquid into the environment surrounding the device.

The device may also be provided with electronic control means that is capable of increasing the power that is applied to the heating means to increase its thermal output and, consequently, increase the rate of emanation of air treatment agent.

The housing is preferably substantially open toward the lower aspect thereof to permit convenient access to, and sight of, a refill when releasably held by the securing means. This arrangement may be advantageous since a user will be able to visually monitor the level of volatile liquid remaining in the refill.

Alternatively, the housing may substantially surround the refill when the refill is held by the securing means. This arrangement may be advantageous as an engaged refill may be less susceptible to being tampered with. Additionally, this arrangement may permit the device to have an improved aesthetic from a consumer perspective.

The securing means may engage any part of the refill to ensure the position of the refill in relation to the device. Preferably the receiving means are arranged to engage with an upper portion of the refill since this arrangement may facilitate a more reliable positioning of the wick within the chimney means.

Alternatively, the receiving means may engage a lower portion of the refill. This arrangement may be particularly useful where the housing is arranged to substantially surround an engaged refill.

As a further alternative the receiving means may be arranged to engage more than one portion of the refill.

The airborne agent detector means is preferably substantially completely isolated from any fluid present in the interior of the housing such that any fluid present in the interior of the housing is substantially completely prevented from passing through said one or more housing walls to be detectable by the airborne agent detector means.

The housing is preferably provided with a concave recess in a wall thereof that extends into the interior of the housing. The concave recess is preferably sized to receive the airborne agent detector means therein. The concave recess may be provided with a cover that is sized to fill the recess and to substantially follow the shape and/or contour of the side wall, and wherein said cover comprises the at least one aperture. In a preferred arrangement the airborne agent detector means is located within the recess and the cover is substantially permanently sealed to the adjacent side walls to substantially completely prevent ingress of any unwanted materials into the recess other than through the aperture(s) in the cover, and even more preferably completely prevent ingress of any unwanted materials into the recess other than through the aperture(s) in the cover.

Providing the airborne agent detector means within the recess in order to substantially completely isolate it from the interior of the housing has been found to be particularly advantageous insofar as the device may be better protected against false detections by said detector means due to the air treatment agent emanated by the device. With many known devices when the air treatment agent is emanated small quantities of the emanated agent are not successfully emanated into the surrounding environment but instead can get trapped within the device or impinge on the housing walls to circulate inside the device and/or pool inside the device and subsequently evaporate within the device. Without the isolation of the detector means the trapped emanated agent is able to interfere with, and in some cases completely saturate, the detector means such that it is rendered almost completely incapable of reading variations in airborne agents in the environment surrounding the device. Exposure to such high levels of detectable material, and particularly prolonged exposure, may also lead to problems associated with loss of sensitivity, detector means contamination, reduction of detector means lifetime and, ultimately, loss of detector means functionality.

The airborne agent detector means may be configured to wirelessly communicate with the control means in order to preserve the integrity of the recess against ingress of trapped emanated air treatment agent. Alternatively, a small conduit into the recess may be provided to permit a wired communication between the airborne agent detector means and the control means wherein any gaps between the conduit and the wire(s) is substantially completely sealed, and preferably completely sealed, to prevent the ingress of trapped emanated air treatment agent into the recess.

The aperture(s) may be provided with a filter membrane to prevent or substantially prevent particulate contamination of the airborne agent detector means whilst allowing gas diffusion therethrough. The filter membrane may be a plastics material with suitable diffusion properties such as a polyethylene membrane.

The housing wall(s) may be provided with an outwardly extending protrusion adjacent to the aperture(s) communicating with the airborne agent detector means in order to prevent an emanated air treatment agent from entering the aperture(s) to falsely trigger the airborne agent detector means and/or saturate the airborne agent detector means. Preferably the outwardly extending protrusion is provided in the form of a cowl located above the aperture(s) the divert any air treatment agent away from the aperture(s).

Preferably the airborne agent detector means comprises at least one odour sensor means. The odour sensor may comprise one or more metal oxide semiconductor sensors and/or one or more metal oxide sensors. The at least one odour sensor means may be combined with one or more additional sensors from the list of: a motion sensor; a person sensor; a light sensor; a sound sensor; a humidity sensor; a smoke sensor; a temperature sensor.

In order for any metal oxide semiconductor/metal oxide odour sensor to be operational the sensor must heat up to an operational temperature to facilitate suitably active surface chemistry on said sensor, typically this temperature is in the order of 300 to 380° C. The need to access such high operation temperatures makes devices containing such sensors consume large amounts of energy. It is a further object of the present invention to improve the energy consumption of devices containing oxide semiconductor/metal oxide odour sensor(s) and to this end the inventors have realised that it is possible to achieve this aim via pulsing the energy applied to said sensor(s).

In one preferred arrangement power is applied to the sensor(s) substantially continuously in order to get the sensor(s) to an operational temperature to ensure that said sensor(s) surface chemistry is suitably active to detect airborne agents and thereafter the power is applied intermittently to the sensor(s) to keep the sensor(s) at or close to an operational temperature and/or to ensure that said sensor(s) surface chemistry is suitably active to detect airborne agents.

In another preferred embodiment after the power has been applied to the sensor(s) substantially continuously to get the sensor(s) to an operational temperature to ensure that said sensor(s) surface chemistry is suitably active to detect airborne agents, thereafter the power is applied intermittently to the sensor(s) to keep the sensor(s) at an operational temperature and/or to ensure that said sensor(s) surface chemistry is suitably active to detect airborne agents such that the odour sensor may substantially continuously or routinely measure the to quantities of airborne agents entering the aperture(s).

In an alternatively preferred embodiment after the power has been applied to the sensor(s) substantially continuously to get the sensor(s) to an operational temperature to ensure that said sensor(s) surface chemistry is suitably active to detect airborne agents, thereafter the power is applied generally intermittently to the sensor(s) to keep the sensor(s) close to an operational temperature and/or to ensure that said sensor(s) surface chemistry is suitably active to detect airborne agents. Within the period of intermittent power application may be periods of continual power application and/or increased power application to temporally place the sensor(s) at the operation temperature and/or to ensure that said sensor(s) surface chemistry is suitably active to detect airborne agents, wherein the odour sensor is arranged to cooperate with this application of power thereto to only measure the quantities of airborne agents entering the aperture(s) when the sensor(s) is at the operational temperature and/or to ensure that said sensor(s) surface chemistry is suitably active to detect airborne agents in the power application cycle.

In a further alternatively preferred embodiment after the power has been applied to the sensor(s) substantially continuously to get the sensor(s) to an operational temperature to ensure that said sensor(s) surface chemistry is suitably active to detect airborne agents, thereafter follows a period of no application of power, wherein the non-application of power is followed by the application of power substantially continually to get the sensor(s) to an operational temperature to ensure that said sensor(s) surface chemistry is suitably active to detect airborne agents, and the cycle continues in accordance with the same pattern throughout the operation of the device.

Preferably the once the metal oxide semiconductor/metal oxide odour sensor to has been heated up to an operational temperature the pulses of power may last for a 5 to 1000 ms period with an off-period lasting between 0.5 to 10 seconds, and more preferably the pulses of power last for a 5 to 250 ms period with an off-period lasting between 0.5 to 7.5 seconds, and even more preferably the pulses of power last for a 5 to 100 ms period with an off-period lasting between 0.5 to 5.5 seconds, and most preferably the pulses of power last for a 5 to 60 ms period with an off-period lasting between 0.5 to 3.5 seconds, ideally the pulses of power last for substantially 35 ms with an off-period lasting for substantially 2.2 seconds.

In the context of the present invention and for the avoidance of doubt "operational temperature" is used in relation to the present invention to relate to the temperatures that the sensor(s) must access to facilitate suitably active surface chemistry on said sensor. For the further avoidance of doubt, in the context of the present invention "close to an operational temperature" is understood to mean the temperature is only permitted to drop below an operation temperature defined by the duration of time (as defined above) that it would take the device under the application of power to the sensor to heat up to an operational temperature. The skilled person would understand the boundaries of "close" to be based on how the system had been tuned when the sensor(s) of the device may be powered 5 to 1000 ms period with an off-period lasting between 0.5 to 10 seconds; such that a temperature would not be defined as "close to an operational temperature" if the sensor was not capable of reaching an operational temperature within the operational boundaries the device was tuned to.

In order to maintain and/or improve the sensitivity of the airborne agent detector means and prevent the false triggering thereof, once a quantity of air treatment agent has been emanated the control means may prevent the airborne detection means from operating for a period of time to allow the initial high concentration of air treatment agent surrounding the device immediately after emanation to subside as the agent emanates further into the surrounding environment in order to prevent false detections of airborne agent by the detector means. Preferably the control means is operable to disable the airborne agent detector means from operating for between 1 second to 30 minutes after emanation, and more preferably 5 seconds to 15 minutes after emanation, and even more preferably 10 seconds to 10 minutes after emanation, and most preferably 15 seconds to 5 minutes after emanation, and ideally for substantially between 90 to 180 seconds after emanation; by virtue of this arrangement the airborne agent detector will also be conserving power consumption which is particularly useful if the device is to be non-mains electric powered. Alternatively the control means may be operable to ignore and/or dismiss signals from the airborne agent detector means for between 1 second to 30 minutes after emanation, and more preferably 5 seconds to 15 minutes after emanation, and even more preferably 10 seconds to 10 minutes after emanation, and most preferably 15 seconds to 5 minutes after emanation, and ideally for substantially between 90 to 180 seconds after emanation.

In order to further maintain and/or improve the sensitivity of the airborne agent detector means the control means may be provided with auto-ranging functionality whereby said functionality is operable to select the correct range of the signals received from the airborne agent detector in order to ensure consistent response is maintained to further airborne agents whilst the detector means is already under the influence of previously existing airborne agent(s) or other environmental factors.

Preferably the at least one airborne agent detector operable, in use, to detect whether the current airborne agent level deviates from a background airborne agent level detected by more than a predetermined amount, wherein the background airborne agent level and the current airborne agent level is calculated by the device, preferably by the control means.

Preferably, the control means are operable to calculate the current airborne agent level by calculating an average of a predetermined number of most recent readings of the airborne agent detector means. Preferably, two to five of the most recent readings, more preferably three of the most recent readings.

The control means may be operable to calculate the deviation of the current airborne agent level from the background level by means of a subtraction of one from the other, and/or by means of a ratio of one to the other.

Preferably, the deviation is calculated by subtracting the background level from the current airborne agent level and dividing that amount by the background level value. The result may be multiplied by a constant, for ease of display and/or use.

Unlike several known prior art devices the device of the present invention does not operate using a pre-defined value for the background airborne agent level, rather the device of the present invention calculates this level and uses this calculated level to control the release of the at least one air treatment agent. This arrangement may be advantageous as the device is operable to adapt how it releases the one or more air treatment agent depending on the characteristics of the surrounding environment in which it is used.

Preferably, the control means are operable to calculate the background airborne agent level by calculating an average of a longer time period than that over which the current airborne agent level is calculated.

Preferably, the background airborne agent level and the current airborne agent level are temporally offset, preferably by at least 5 seconds, more preferably by at least 10 second, more preferably by at least 20 seconds.

Once the device is placed into an operational mode, the background airborne agent level may be an average of the levels of airborne agent detected by the device throughout the duration of that operational mode. In this arrangement the device may better 'learn' the characteristics of its local environment and, during use, will be better able to provide for the release of an air treatment agent(s) when the current airborne agent level deviates from the background level by more than the predetermined amount. If a user wishes to move the device to an alternative location, a user may be encouraged to reset the device from the operational mode, this resetting of the device may have the effect of zeroing the average levels of background agent such that the device is operable to 'learn' the characteristics of its new environment when placed back into the operational mode by calculating the average background agent level from no existing starting point.

Preferably, the control means are operable to calculate the background airborne agent level by calculating an average of a predetermined number of some or all of the most recent readings of the detector. Preferably 10 to 10,000 of the most recent readings, more preferably 20 to 5,000 of the most recent readings, and most preferably 50 to 1000 of the most recent readings.

The device may be provided with an initial setting mode wherein when the device is first powered up, the control means will automatically calibrate based on the existing background odour when the device is first switched on.

In an alternative or additional arrangement, the control means are preferably operable to calculate the background level based on calculating a series of averages from rolling windows of measurements from the airborne agent detector means. Each rolling window may be an average of between two and ten readings, preferably six readings. Preferably, the windows do not overlap. Preferably, the windows span a time period of between 5 and 30 minutes, preferably between 10 and 25 minutes, preferably between 15 and 20 minutes. There may be approximately 30 to 50 windows.

Preferably, the control means are operable to discard the oldest window when a new window becomes available, preferably taking into account an offset between the current and background levels.

Preferably, the control means are operable to adjust the predetermined level of deviation from the background level that results in air treatment agent being released. The predetermined level may be manually adjustable. The deviation may be a positive or negative deviation.

Where the airborne agent detector means is provided in the form of one or more metal oxide semiconductor/metal oxide odour sensor said sensor(s) may be provided with one or more resistors in series therewith to ensure a consistent output of signal from the sensor(s) as their resistance changes during their operation in response to their detection of airborne agent. Preferably the device is provided with between 3 to 5 dynamic range resistors with a 1 to 300KΩ range.

The device is preferably provided with one exit orifice per replaceable refill of air treatment agent secured in the device, this arrangement is preferably to prevent cross-contamination of the air treatment agents.

Preferably the container of air treatment agent is received entirely within the housing of the device.

The device may be provided with a user-controlled boost mechanism. In use of the device, the activation of said boost mechanism may substantially immediately cause the dispensing of the at least one air treatment agent.

The airborne agents detected by the airborne agent detector means may be common household odours (and the chemicals which constitute) these malodours. For example: kitchen malodour; bathroom malodour; tobacco smoke; pet odours; mould and/or mildew; body odour; fish; onions; garbage; fragrance from other products (such as detergents, polishes, cleaning products etc). To facilitate such detection the odour sensor means may be operable to detect at least some of the following chemical components: amines and nitrogen compounds; acids and/or sulphur compounds, such as mercaptans, thioacids, thioesters, sulfides, phenols and skatole odours.

The device of any of the above-mentioned aspects may be provided with an indicator wherein said indicator is operable to indicate to a user what function the device is currently performing. The indicator may be operable to provide a visual indication and/or provide an audible indication.

Preferably the indicator is configured to provide a visual indication by emitting light from one or more light sources, preferably one or more LEDs.

The one or more light sources may be adapted to emit a different colour of light to indicate the current function the device is performing. Additionally or alternatively, the one or more light sources may blink or flash to indicate the current function the device is performing.

Alternatively or additionally, the device may be operable to visually indicate the function currently being performed by the device via a screen. The screen may be an LCD screen that is adapted to provide a message to a user, for instance such messages could include "ON", "SENSING", "MOTION DETECTED", "RESTING", "NORMAL MODE", "DETECTION MODE", "OFF".

According to a second aspect of the present invention there is provided therefore a device for evaporating a volatile air treatment agent, the device comprising:

a housing with at least one exit orifice for evaporated air treatment agent to exit the device;

receiving means within said housing to releasably receive and secure a refill to the device;

electrical heating means within said housing;

control means; and chimney means within said housing having a lower orifice and an upper orifice to define a first airflow channel therebetween;

an airborne agent detector means operable to detect airborne agents in the air, wherein said means are provided with at least one aperture to the exterior of the device to permit, in use, air from outside of the device to enter said airborne agent detector means;

wherein device further comprises a replaceable refill engaged with the receiving means, wherein said refill comprises:

a reservoir portion for holding a quantity of volatile air treatment agent; and a wick having a proximal end within the reservoir portion substantially adjacent a base of said reservoir portion and having a distal end extending above the reservoir portion;

the device being characterised in that a second airflow channel is provided between said at least one aperture of the airborne agent detector means and said exit orifice.

Any of the features described herein may be combined with any of the above aspects in any combination.

DESCRIPTION OF AN EMBODIMENT

Embodiments of the invention will now be described, by way of example only, with reference to the following drawings in which.

Figures 1, 2, 3, 4:
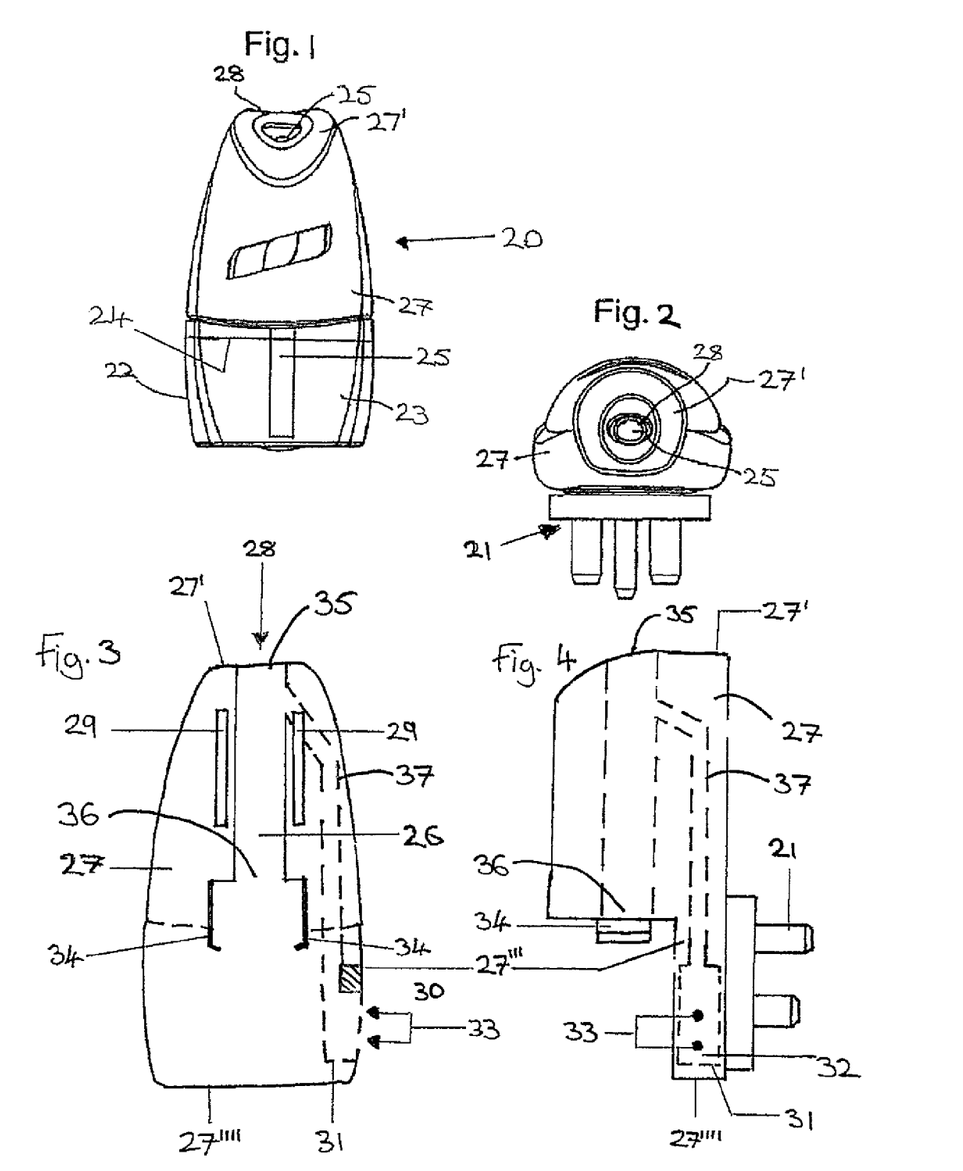
FIG. 1 illustrates a front elevation of a plug-in electrical device according to the present invention.
FIG. 2 illustrates a top elevation of the plug-in electrical device according to the present invention.
FIG. 3 illustrates a cross sectional view of the plug-in electrical device according to the present.
FIG. 4 illustrates a side elevation of a plug-in electrical device according to the present invention.

FIGS. 1-4 illustrate a device 20 according to the present invention, specifically the device 20 is a plug-in device intended to be connected to a mains electricity socket, the device being mounted on or carried by a electrical plug formations 21 that extend out of the rear side of the device 20. The device 20 is illustrated in FIGS. 1 & 2 with a refill 22 of volatile liquid air treatment agent engaged therewith, held in place by receiving means 34. The refill 22 has a reservoir portion 23 in the form of a glass bottle containing the air treatment agent 24 and a wick 25 extending from the reservoir 23 to above the top of the bottle through a seal (not shown) and into a chimney means 26 of the device 20. The wick 25 may be substantially cylindrical and the seal is present to retain the air treatment agent 24 within the bottle should the device 20 be knocked over and/or inverted when the refill 22 is engaged therewith.

The device 20 has a housing 27 which partially extends over an upper part of the refill 22. The top of the housing 27 has a generally circular central exit orifice 28 which is aligned with an upper orifice 35 of the chimney means 26. The chimney means 26 between its lower orifice 36 and upper orifice 35 defines the first airflow channel therebetween. Air is capable of flowing between the seal (not shown) and the lower orifice 36, driven in part by heat radiating from the heating means 29, toward the upper orifice 35 and out of the exit orifice 28.

The heating means 29 are illustrated as resistors, such as positive temperature coefficient (PTC) thermistors but said means could be provided by way of a ring heater or the like, or a combination thereof.

Although not illustrated, the device 20 may be provided with means to receive at least two separate containers of liquid 22. In this arrangement the device 20 may be provided with additional heating means to cause the emanation of the air treatment agent 24.

Most preferably the top wall 27' of the housing 27 is angled such it slopes downwardly toward the front wall 27" and the exit orifice 28 is provided in the top wall 27'. In use, to be discussed in more detail below, air treatment agent 24 emanated from the device 20 is directed in a generally upward direction or a generally upward and forward direction perpendicular to the slope of the top wall 27'.

The airborne agent detector means 30 is provided in the side wall 27''' generally adjacent the bottom wall 27'''' of the housing 27 located within dotted lines as said detector means 30 is substantially completely isolated from the interior of the housing such that any air treatment agent erroneously present in the interior of the housing is substantially completely prevented from passing through the housing walls to be detectable by the detector means 30.

The housing 27 is provided with a recess 31 that extends into the interior of the housing 27, the recess 31 being sized to receive the airborne agent detector means 30 therein and have a second airflow channel 37 extending therefrom. The recess is provided with a cover 32 that is sized to fill the recess to and substantially follow the shape and/or contour of the exterior-facing side wall 27'''. The cover 32 is provided with at least one aperture 33 to permit air outside of the device 20 to enter and its content be analysed by the detector means 30. The airborne agent detector means 30 is located within the recess 31 and the cover 32 is substantially permanently sealed to the adjacent side wall 27''' to substantially completely prevent ingress of any unwanted materials into the recess other than through the aperture 33 in the cover 32.

The second airflow channel 37 is substantially completely separate from the majority of the first airflow channel such that the intersection of the two airflow channels is adjacent to the exit orifice.

Although not illustrated the second airflow channel could be substantially contiguous with the first airflow channel, such that the intersection between the two airflow channels is at or adjacent to the lower orifice 36.

Again, although not illustrated as a further alternative the second airflow channel 37 may be completely separate from and does not intersect with the first airflow channel, wherein said second airflow channel only permits the passage of air between said at least one aperture of the airborne agent detector means and said exit orifice.

Yet again, although not illustrated the second airflow channel 37 may be completely separate from and does not intersect with the first airflow channel, wherein said second airflow channel is present to only encourage the passage of air through said at least one aperture 33 and past said airborne agent detector means 30 and into the interior of the housing 27. In this arrangement there is no defined second airflow channel 27 within the device once the airflow has passed the airborne agent detector means 30, such that the airflow is left to find its own way through the device toward the exit orifice.

Any or all of the above-mentioned arrangements may be advantageous as the second airflow channel may permit a greater quantity of air to be drawn into and/or past the airborne agent detector means such that it is able to analyse a broader cross-section of the air surrounding the device to determine whether it is appropriate to emanate or increase the emanation rate of air treatment agent from the refill. During the operation of the device, the heat emitted in emanating the air treatment agent may also assist in driving airflow through the second airflow channel.

The second airflow channel 37 may be provided with a tortuous pathway (not shown) at or adjacent its intersection with the first airflow channel or at or adjacent the exit orifice 28 such that any air treatment agent condensing in said second airflow channel 37 will not be permitted to travel down the channel toward to the airborne agent detector means 30 and risk the possible contamination and/or saturation thereof.

The second airflow channel 37 may be provided with a filter membrane (not shown) at or adjacent its upper extremity such as at its intersection with the first airflow channel or at or adjacent the exit orifice 28, wherein said filter membrane is configured to prevent or substantially prevent particulate contamination of the airborne agent detector means 30 whilst allowing gas diffusion therethrough such that any air treatment agent condensing in or near said second airflow channel 37 will not be permitted to travel down the channel 37 toward to the airborne agent detector means 30 and risk the possible contamination and/or saturation thereof.

The device 20 is arranged such that the airborne agent detector means 30 is substantially completely isolated from the interior of the housing and this is considered to be advantageous insofar as the device may be better protected against false detections by said detector means 30 due to the air treatment agent erroneously and/or routinely being emanated by the device 20 within the interior of the housing. A small conduit (not shown) into the recess is provided to permit a wired communication between the airborne agent detector means 30 and a control means (not shown), the gap between the conduit and the wire(s) is sealed to prevent the ingress of trapped emanated air treatment agent into the recess such as with resin or adhesive or the like. Although not illustrated, the airborne agent detector means 30 could wirelessly communicate with the control means in order to preserve the integrity of recess 31 against ingress of air treatment agent 24 present in the interior of the housing.

Although not illustrated the aperture 33 can be filled with a filter membrane to prevent or substantially prevent particulate contamination of the airborne agent detector means whilst allowing gas diffusion therethrough. The filter membrane may be a plastics material with suitable diffusion properties such as a poly ethylene membrane.

The airborne agent detector means 30 generally comprises at least one odour sensor means, and preferably one or more metal oxide semiconductor sensors and/or one or more metal oxide sensors.

The mode of operation of the device 20 and the interrelation of the components will now be explained.

In order for any metal oxide semiconductor/metal oxide odour sensor to be operational the sensor must heat up to an operational temperature, typically this temperature is in the order of 300 to 350° C. The device 20 may be arranged such that its control means allows power to be applied to the sensor(s) substantially continuously in order to get the sensor(s) to an operational temperature and thereafter the power is applied intermittently to the sensor(s) to keep the sensor(s) at, or close to, an operational temperature such that the odour sensor may substantially continuously or routinely measure the to quantities of airborne agents entering the aperture 14, 33.

Once the metal oxide semiconductor/metal oxide odour sensor to has been heated up to an operational temperature the pulses of power may last for a 5 to 1000 ms period with an off-period lasting between 0.5 to 10 seconds, and more preferably the pulses of power last for a 5 to 250 ms period with an off-period lasting between 0.5 to 7.5 seconds, and even more preferably the pulses of power last for a 5 to 100 ms period with an off-period lasting between 0.5 to 5.5 seconds, and most preferably the pulses of power last for a 5 to 60 ms period with an off-period lasting between 0.5 to 7.5 seconds, ideally the pulses of power last for substantially 35 ms with an off-period lasting for substantially 2.2 seconds.

To improve and/or maintain the sensitivity of the airborne agent detector means 30 and prevent the false triggering thereof, once a quantity of air treatment agent has been emanated and/or a higher rate of emanation has been maintained for a predefined period the control means prevents the airborne detection means 30 from operating for a period of time to allow the initial high concentration of air treatment agent surrounding the device immediately after emanation to subside as the agent emanates further into the surrounding environment in order to prevent false detections of airborne agent by the detector means 30. Preferably the control means is operable to disable the airborne agent detector means 30 from operating for between 1 second to 30 minutes after emanation, and more preferably 5 seconds to 15 minutes after emanation and/or higher rate of emanation, and even more preferably 10 seconds to 10 minutes after emanation and/or higher rate of emanation, and most preferably 15 seconds to 5 minutes after emanation and/or higher rate of emanation, and ideally for substantially 100 seconds after emanation and/or higher rate of emanation.

In use the control means is arranged to analyse signals received from the airborne agent detector means 30 to detect whether the current airborne agent level deviates from a background airborne agent level detected by more than a predetermined amount, wherein the background airborne agent level and the current airborne agent level is calculated by said control means.

The control means are operable to calculate the current airborne agent level by calculating an average of a predetermined number of most recent readings of the airborne agent detector means 30. Preferably, two to five of the most recent readings, more preferably three of the most recent readings.

The control means may be operable to calculate the deviation of the current airborne agent level from the background level by means of a subtraction of one from the other, and/or by means of a ratio of one to the other.

Preferably however, the deviation is calculated by subtracting the background level from the current airborne agent level and dividing that amount by the background level value. The result may be multiplied by a constant, for ease of display and/or use.

The control means are operable to calculate the background airborne agent level by calculating an average of a longer time period than that over which the current airborne agent level is calculated. To improve the sensitivity the background airborne agent level and the current airborne agent level are temporally offset, preferably by at least 5 seconds, more preferably by at least 10 second, more preferably by at least 20 seconds.

Once the device 20 is placed into an operational mode, the background airborne agent level may be an average of the levels of airborne agent detected by the device throughout the duration of that operational mode. In this arrangement the device 20 may better 'learn' the characteristics of its local environment and, during use, will be better able to provide for the release of an air treatment agent(s) when the current airborne agent level deviates from the background level by more than the predetermined amount.

If a user wishes to move the device 20 to an alternative location, a user may be encouraged to reset the device from the operational mode, this resetting of the device may have the effect of zeroing the average levels of background agent such that the device is operable to 'learn' the characteristics of its new environment when placed back into the operational mode by calculating the average background agent level from no existing starting point.

The control means are operable to calculate the background airborne agent level by calculating an average of a predetermined number of some or all of the most recent readings of the detector, preferably 10 to 10,000 of the most recent readings.

The device 20 may be provided with an initial setting mode wherein when the device is first powered up, the control means will automatically calibrate based on the existing background odour when the device is first switched on. Thereafter the control means are operable to calculate the background level based on calculating a series of averages from rolling windows of measurements from the airborne agent detector means. Each rolling window may be an average of between two and ten readings, preferably six readings. Preferably, the windows do not overlap.

Preferably, the windows span a time period of between 5 and 30 minutes, preferably between 10 and 25 minutes, preferably between 15 and 20 minutes. There may be approximately 30 to 50 windows. The control means are operable to discard the oldest window when a new window becomes available, preferably taking into account an offset between the current and background levels.

Preferably, the control means are operable to adjust the predetermined level of deviation from the background level that results in air treatment agent being released. The predetermined level may be manually adjustable. The deviation may be a positive or negative deviation.

Where the airborne agent detector means is provided in the form of one or more metal oxide semiconductor/metal oxide odour sensor said sensor(s) may be provided with one or more resistors in series therewith to ensure a consistent output of signal from the sensor(s) as their resistance changes during their operation in response to their detection of airborne agent. Preferably the device is provided with between 3 to 5 dynamic range resistors with a 1 to 300KΩ range.

The device 20 may be provided with a user-controlled boost mechanism (not shown). In use of the device, the activation of said boost mechanism may substantially immediately cause the dispensing of the at least one air treatment agent and/or higher rate of emanation.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A device adapted to evaporate a volatile air treatment agent from a replaceable refill, the device comprising:
   a housing with at least one exit orifice for evaporated air treatment agent to exit the device;
   receiving means within said housing to releasably receive and secure the refill to the device;
   electrical heating means within said housing;
   control means; and
   chimney means within said housing having a lower orifice and an upper orifice to define a first airflow channel therebetween;
   an airborne agent detector means which includes at least one odour sensor means having one or more metal oxide semiconductor sensors/and or one or more metal oxide sensors, which airborne agent detector means is operable to detect airborne agents in the air, wherein said means are provided with at least one aperture to the exterior of the device to permit, in use, air from outside of the device to enter said airborne agent detector means;
   wherein the refill for use with the device comprises:
   a reservoir portion for holding a quantity of volatile air treatment agent; and
      a wick having a proximal end within the reservoir portion substantially adjacent a base of said reservoir portion and having a distal end extending above the reservoir portion;
      and wherein the device is configured such that, in use, the securing means are adapted to hold the refill such that the distal end of the wick is located within the chimney means;
      characterised in that:
      a second airflow channel is provided between said at least one aperture of the airborne agent detector means and said exit orifice.

2. A device according in to claim 1, wherein the housing comprises a bottom wall, a top wall remote therefrom and one or more side walls therebetween, and wherein the exit orifice(s) is provided in the top wall and/or in the side wall(s) at a position substantially adjacent to the top wall and wherein the at least one aperture for the airborne agent detector means is spaced away from the exit orifice(s).

3. A device according to claim 1, wherein the at least one aperture is located in the side wall(s) or rear wall of the housing adjacent or substantially adjacent to the bottom wall.

4. A device according to claim 1 wherein the second airflow channel is substantially completely separate from the first airflow channel, such that to the extent that there is any intersection of the two airflow channels said intersection is at or adjacent to the upper orifice.

5. A device according to claim 1, wherein the second airflow channel is substantially contiguous with the first airflow channel, such that the intersection between the two airflow channels is at or adjacent to the lower orifice.

6. A device according to claim 1, wherein the second airflow channel is completely separate from and does not intersect with the first airflow channel, wherein said second airflow channel only permits the passage of air between said at least one aperture of the airborne agent detector means and said exit orifice.

7. A device according to claim 1, wherein the second airflow channel is completely separate from and does not intersect with the first airflow channel, wherein said second airflow channel is present to only encourage the passage of air through said at least one aperture of the airborne agent detector means and past said airborne agent detector means and into the interior of the housing.

8. A device according to claim 1, wherein the second airflow channel is provided with a tortuous pathway at or adjacent its intersection with the first airflow channel or at or adjacent the exit orifice such that any air treatment agent condensing in said second airflow channel will not be permitted to travel down the channel toward to the airborne agent detector means.

9. A device according to claim 1, wherein the second airflow channel is provided with a filter membrane at or adjacent its upper extremity such as at its intersection with the first airflow channel or at or adjacent the exit orifice, wherein said filter membrane is configured to prevent or substantially prevent particulate contamination of the airborne agent detector means whilst allowing gas diffusion therethrough.

10. A device according to claim 1, wherein the device is provided with more than one airborne agent detector means and said plurality of detector means are spaced apart from each other within the housing, and wherein a respective airflow channel is provided for each of said detector means.

11. A device according to claim 1, wherein the exit orifice of the housing is the upper orifice of the chimney means.

12. A device according to claim 1, wherein the heating means is located adjacent the chimney means and said chimney means is provided with cut-out portions in registration with the heating means to permit, in use, heat from said means to enter the channel and increase the airflow therethrough.

13. A device according to claim 1, wherein the second airflow channel is provided with a cut-out portion adjacent to the heating means to permit, in use, heat from said means to enter the channel and increase the airflow therethrough.

14. A device according to claim 1, wherein the device is provided with variance means that directly or indirectly engage or communicate with the chimney means to permit the rotation thereof to permit a user of the device to rotate the chimney means in order to alter, in use, the temperature applied from the heating means to the wick of the refill.

15. A device according to claim 1, wherein the device is provided with electronic control means that is capable of increasing the power that is applied to the heating means to increase its thermal output.

16. A device according to claim 1, wherein the airborne agent detector means is substantially completely isolated from any fluid present in the interior of the housing such that any fluid present in the interior of the housing is substantially completely prevented from passing through said one or more housing walls to be detectable by the airborne agent detector means.

17. A device according to claim 1, wherein the housing wall(s) is/are provided with an outwardly extending protrusion adjacent to the aperture(s) communicating with the airborne agent detector means.

18. A device according to claim 1, wherein, in use, energy applied to said metal oxide semiconductor/metal oxide odour sensor(s) is pulsed.

19. A device according to claim 1, wherein, in use, power is applied to the sensor(s) substantially continuously to get the sensor(s) to an operational temperature, thereafter the power is applied intermittently to the sensor(s) to keep the sensor(s) at an operational temperature.

20. A device according to claim 1, wherein, in use, power is applied to the sensor(s) substantially continuously to get the sensor(s) to an operational temperature, thereafter the power is applied intermittently to the sensor(s) to keep the sensor(s) close to an operational temperature.

21. A dispensing device according to claim 1, wherein, in use, power is applied to the sensor(s) substantially continuously to get the sensor(s) to an operational temperature, thereafter followed by a period of no application of power, wherein the non-application of power is followed by the application of power substantially continually to get the sensor(s) to an operational temperature, and the resultant cycle continues thereafter throughout the operation of the device.

22. A device according to claim 1, wherein, in use, once the metal oxide semiconductor/metal oxide odour sensor has been heated up to an operational temperature the pulses of power lasts for a 5 to 1000 ms period with an off-period lasting between 0.5 to 10 seconds.

23. A device according to claim 1, wherein, in use, once the metal oxide semiconductor/metal oxide odour sensor has been heated up to an operational temperature the pulses of power lasts for a 5 to 250 ms period with an off-period lasting between 0.5 to 7.5 seconds.

24. A device according to claim 1, wherein, in use, once the metal oxide semiconductor/metal oxide odour sensor has been heated up to an operational temperature the pulses of power lasts for a 5 to 100 ms period with an off-period lasting between 0.5 to 5.5 seconds.

25. A device according to claim 1, wherein, in use, once the metal oxide semiconductor/metal oxide odour sensor has been heated up to an operational temperature the pulses of power lasts for substantially 35 ms with an off-period lasting for substantially 2.2 seconds.

26. A device according to claim 1, wherein, in use, once a quantity of air treatment agent has been emanated and/or the rate of emanation increased the control means prevents the airborne detection means from operating for a period of time.

27. A device according to claim 26, wherein, in use, the control means is operable to disable the airborne agent detector means from operating for between 1 second to 30 minutes after emanation.

28. A device according to claim 26, wherein, in use, the control means is operable to disable the airborne agent detector means from operating for substantially 100 seconds after emanation.

29. A dispensing device according to claim 1, wherein, in use, the at least one airborne agent detector is operable to detect whether the current airborne agent level deviates from a background airborne agent level detected by more than a predetermined amount, wherein the background airborne agent level and the current airborne agent level is calculated by the device.

30. A dispensing device according to claim 29, wherein, in use, the control means are operable to calculate the current airborne agent level by calculating an average of a predetermined number of most recent readings of the airborne agent detector means.

31. A device for evaporating a volatile air treatment agent, the device comprising:
- a housing with at least one exit orifice for evaporated air treatment agent to exit the device;
- receiving means within said housing to releasably receive and secure a refill to the device;
- electrical heating means within said housing;
- control means; and
- chimney means within said housing having a lower orifice and an upper orifice to define a first airflow channel therebetween;
- an airborne agent detector means which includes at least one odour sensor means having one or more metal oxide semiconductor sensors/and or one or more metal oxide sensors, which airborne agent detector means is operable to detect airborne agents in the air, wherein said means are provided with at least one aperture to the exterior of the device to permit, in use, air from outside of the device to enter said airborne agent detector means;
- wherein device further comprises a replaceable refill engaged with the receiving means, wherein said refill comprises:
- a reservoir portion for holding a quantity of volatile air treatment agent; and;
- a wick having a proximal end within the reservoir portion substantially adjacent a base of said reservoir portion and having a distal end extending above the reservoir portion;

the device being characterised in that:
- a second airflow channel is provided between said at least one aperture of the airborne agent detector means and said exit orifice.

* * * * *